United States Patent
Addison et al.

(10) Patent No.: US 9,826,905 B2
(45) Date of Patent: Nov. 28, 2017

(54) USING COLORED PROBES IN PATIENT MONITORING

(75) Inventors: Paul Stanley Addison, Edinburgh (GB); James Watson, Dunfermline (GB); Rakesh Sethi, Vancouver (CA)

(73) Assignee: Nellcor Puritan Bennett Ireland, Galway (IE)

( * ) Notice: Subject to any disclaimer, the term of this patent is extended or adjusted under 35 U.S.C. 154(b) by 1954 days.

(21) Appl. No.: 12/437,296

(22) Filed: May 7, 2009

(65) Prior Publication Data
US 2010/0286494 A1 Nov. 11, 2010

(51) Int. Cl.
*A61B 5/00* (2006.01)
*A61B 5/1455* (2006.01)
*A61B 5/024* (2006.01)
*A61B 5/08* (2006.01)

(52) U.S. Cl.
CPC .......... *A61B 5/0059* (2013.01); *A61B 5/1455* (2013.01); *A61B 5/726* (2013.01); *A61B 5/024* (2013.01); *A61B 5/0816* (2013.01)

(58) Field of Classification Search
CPC .................................................. A61B 5/1455
USPC ................ 600/310, 322–328, 431, 476, 483, 600/500–505
See application file for complete search history.

(56) References Cited

U.S. PATENT DOCUMENTS

| | | | |
|---|---|---|---|
| 5,490,523 A * | 2/1996 | Isaacson et al. | 600/323 |
| 5,924,982 A | 7/1999 | Chin | |
| 6,599,251 B2 | 7/2003 | Chen et al. | |
| 2006/0258921 A1 * | 11/2006 | Addison et al. | 600/323 |
| 2007/0068527 A1 * | 3/2007 | Baker, Jr. | 128/204.23 |
| 2008/0221418 A1 * | 9/2008 | Al-Ali et al. | 600/324 |
| 2009/0054767 A1 | 2/2009 | Telischak | |
| 2009/0105605 A1 * | 4/2009 | Abreu | 600/549 |
| 2009/0326386 A1 | 12/2009 | Sethi et al. | |
| 2009/0326393 A1 | 12/2009 | Sethi et al. | |
| 2009/0326402 A1 | 12/2009 | Addison et al. | |
| 2010/0076319 A1 * | 3/2010 | Mannheimer et al. | 600/476 |

(Continued)

OTHER PUBLICATIONS

Oxford Dictionary Definition: sensor.*
International Search Report PCT/GB2010/000888, 3 pages, mailed Jul. 23, 2010.

*Primary Examiner* — Puya Agahi
(74) *Attorney, Agent, or Firm* — Haley Guiliano LLP

(57) ABSTRACT

The present disclosure provides a sensor with color-coded indications that various patient physiological parameters are being monitored, such as blood oxygen saturation, blood pressure, respiration rate, and respiration effort. The sensor may sense a physical characteristic used to monitor the physiological parameter, and a visible light emitter emits visible light of a first color that is color-coded to the physiological parameter, but is not used to sense the physical characteristic. The visible light emitter may emit visibly flashing light in response to the sensor sensing a threshold value of the physical characteristic. The sensor may include a second light emitter that may sense the physical characteristic, and may emit light of a second color that is color-coded to a first or second physiological parameter. In some embodiments, the first and second colors may visibly mix. The first and second visible light emitters may emit light independently, including visibly flashing light.

13 Claims, 12 Drawing Sheets

(56) References Cited

U.S. PATENT DOCUMENTS

2010/0079279 A1\* 4/2010 Watson et al. ............... 340/540
2010/0081892 A1 4/2010 Sethi et al.

\* cited by examiner

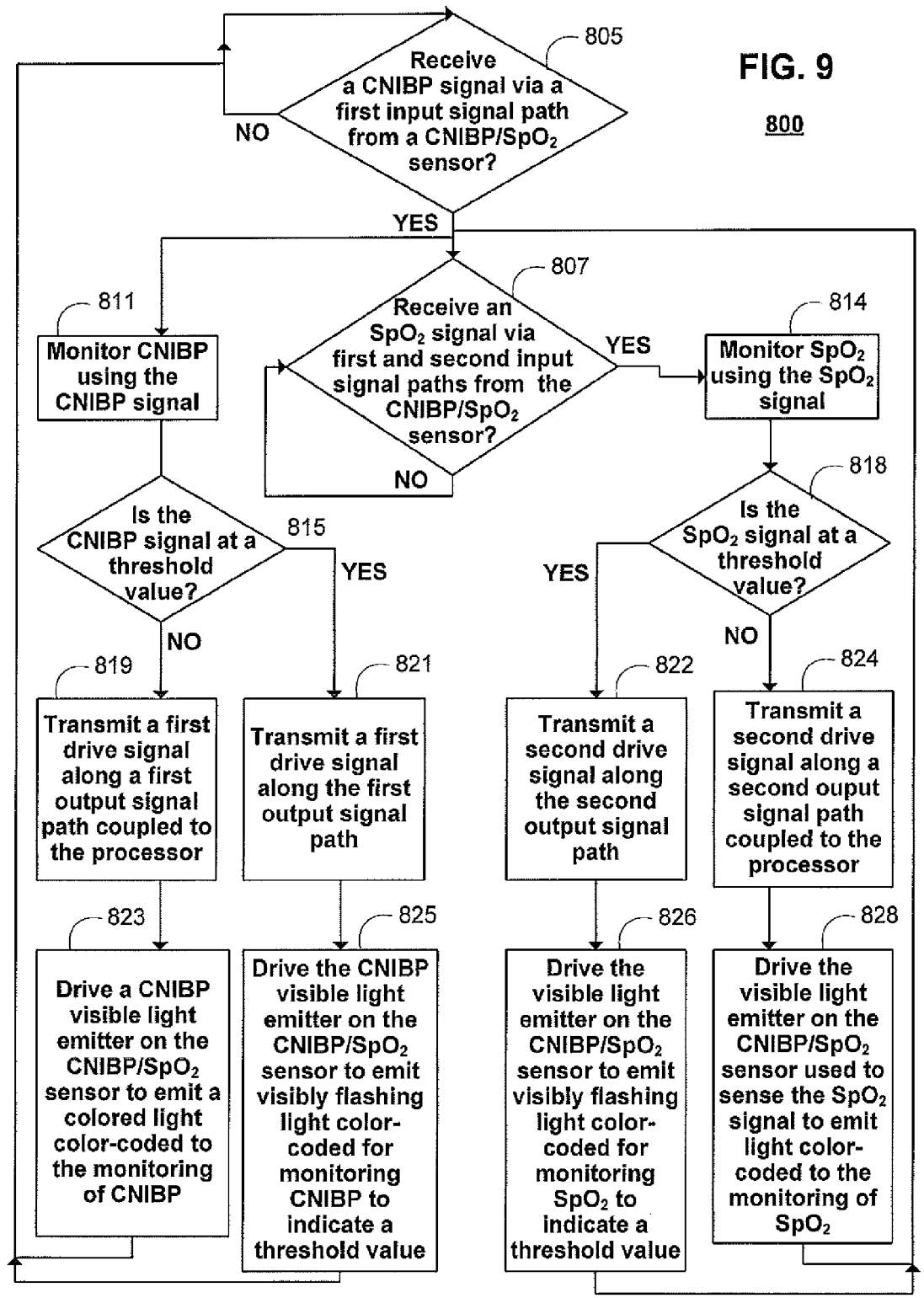

US 9,826,905 B2

USING COLORED PROBES IN PATIENT MONITORING

SUMMARY

The present disclosure relates to patient monitoring, and more particularly, relates to a sensor that provides color-coded indications that various physiological parameters are being monitored, such as blood oxygen saturation, blood pressure, respiration rate, and respiration effort.

In an embodiment, a sensor for monitoring at least one physiological parameter of a patient is provided. The physiological parameter may include blood oxygen saturation, blood pressure, respiration rate, and respiration effort. The sensor may include a support structure and a sensor component coupled to the support structure. The sensor component senses a physical characteristic of the patient used to monitor the at least one physiological parameter. The sensor component includes an infrared light emitter used to sense the first physical characteristic, a detector for detecting the infrared light after it passes within the tissue of the patient, and a first visible light emitter, coupled to the support structure, that emits visible light of a first color. The first visible light emitter is not used to sense the first physical characteristic, and the first color is color-coded to the at least one physiological parameter. The first visible light emitter may emit visibly flashing light in response to the sensor sensing a threshold value of the physical characteristic. In some embodiments, the sensor component may include a second light emitter that may be used to sense the first physical characteristic and/or a second physical characteristic, but may or may not emit visible light. In some embodiments, the second light emitter may not sense a physical characteristic, but may emit light of a second color that is different from the first color. In some embodiments, the second color may be color-coded to the first physiological parameter or a second physiological parameter. In some embodiments, the first and second colors may visibly mix when both of the first and second physiological parameters are being monitored. The third color may be color-coded to the monitoring of the combination of physiological parameters. The second visible light emitter may emit light, including visibly flashing light, independently of the first visible light emitter.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 9 illustrates a process performed in accordance with some embodiments.

DETAILED DESCRIPTION

Figure 1:
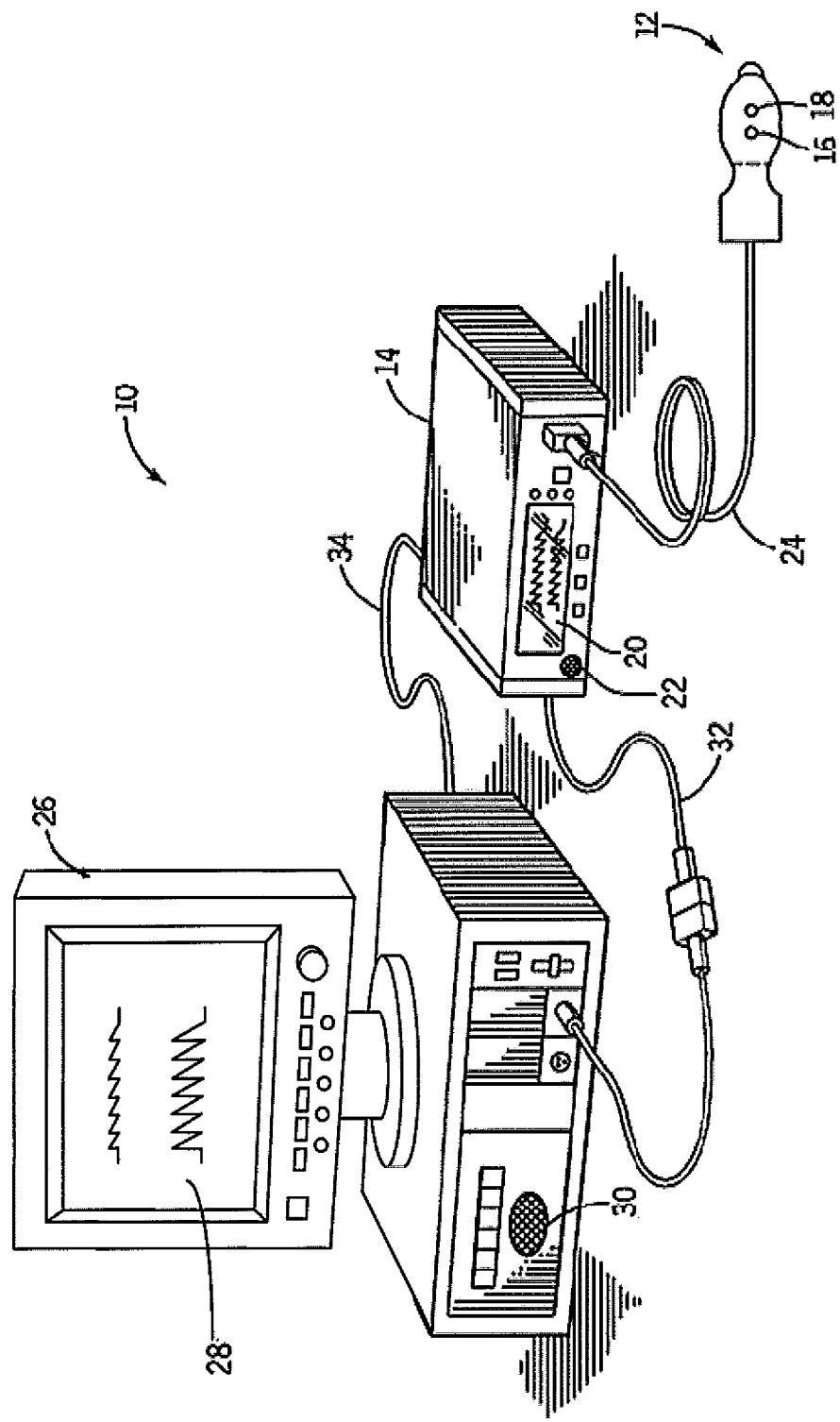
FIG. 1 shows an illustrative pulse oximetry system in accordance with an embodiment.

This disclosure generally relates to providing a visible indication that a physiological parameter (e.g., blood pressure, blood oxygen saturation, respiration rate, respiration effort) is being monitored, and the physiological parameter may be determined from a physical characteristic (e.g., pulsatility of blood in a patient's arteries, attenuation of light in a patient's tissue, or a time-domain photoplethysmograph (PPG) signal) of a patient sensed by a sensor. It should be understood that the received PPG signal may be digital and that the PPG signal may also be generated by any other suitable device(s) capable of generating a PPG or any plethysmograph signal.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the PPG signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t)=[I(t_2,\lambda_{IR})-I(t_1,\lambda_{IR})]I(t_1,\lambda_R)$$

$$y(t)=[I(t_2,\lambda_R)-I(t_1,\lambda_R)]I(t_1,\lambda_{IR})$$

$$y(t)=Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28. In the embodiment shown, multi-parameter patient monitor 26 may also include a speaker 30 similar to speaker 22 described above.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
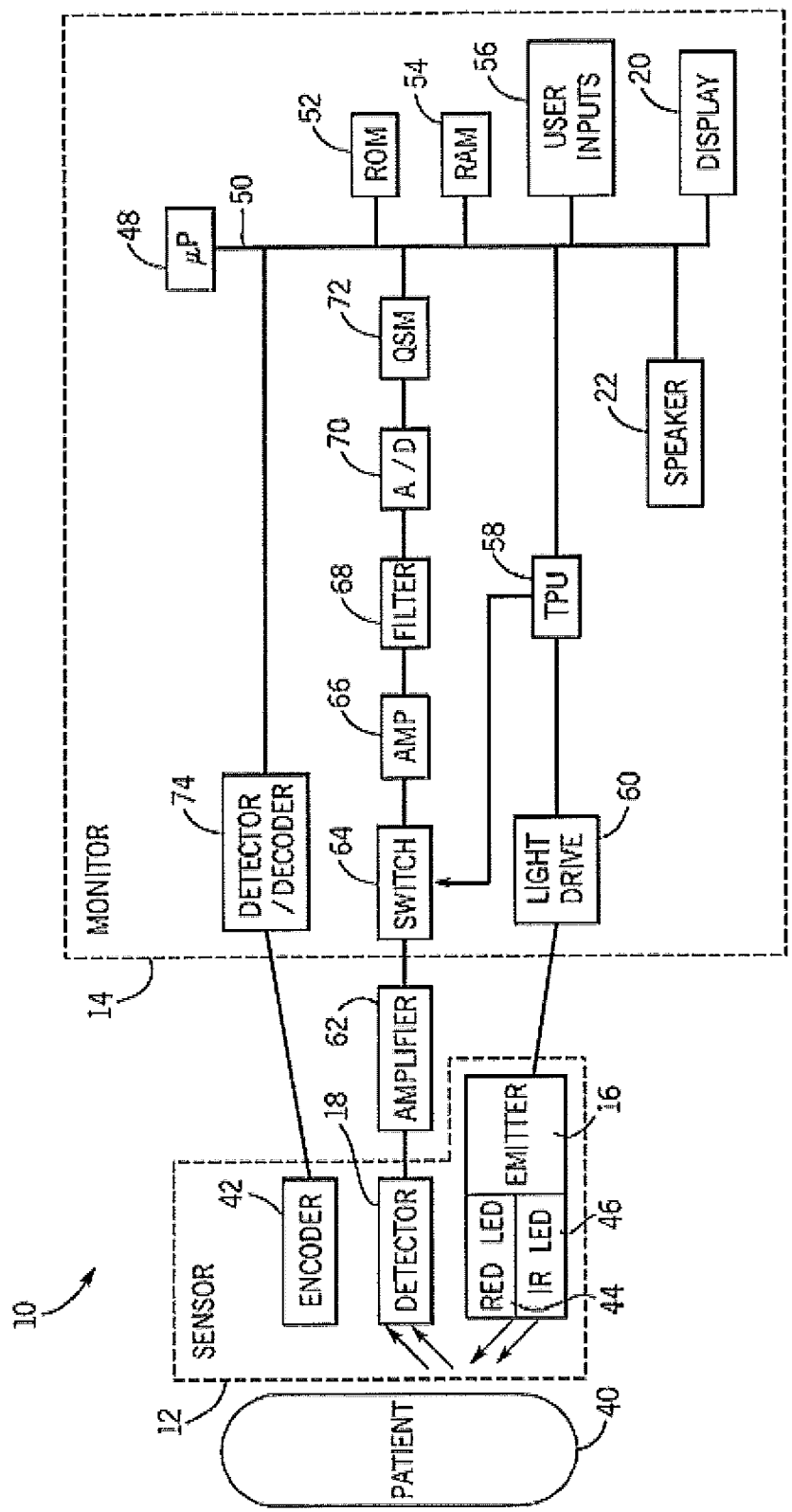
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patients tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \quad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \quad (10)$$

where '||' is the modulus operator. The scalogram may be rescaled for useful purposes. One common rescaling is defined as $$S_R(a, b) = \frac{|T(a, b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unsealed wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{-1/4}(e^{i2\pi f_0 t}-e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \tag{14}$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figures 3A, 3B:
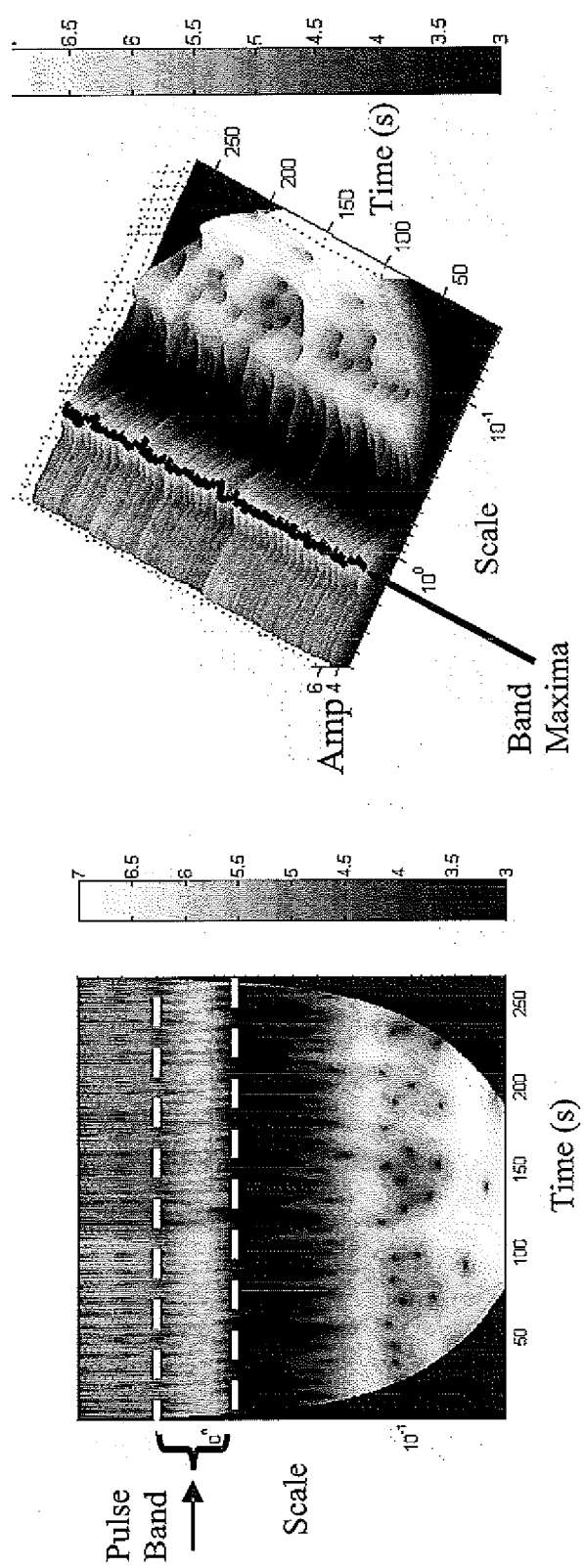
FIGS. 3(a) and 3(b) show illustrative views of a scalogram derived from a PPG signal in accordance with an embodiment.

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
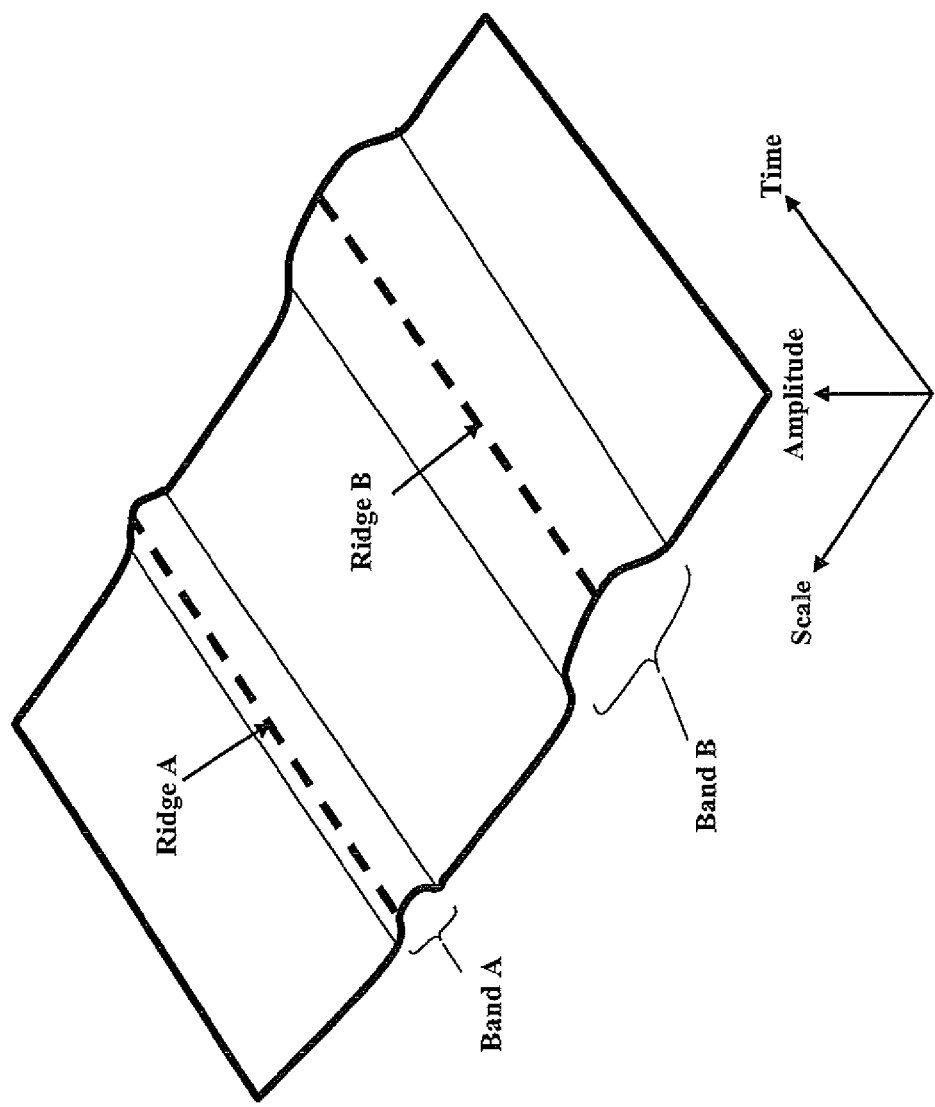
FIG. 3(c) shows an illustrative scalogram derived from a signal containing two pertinent components in accordance with an embodiment.
Figure 3D:
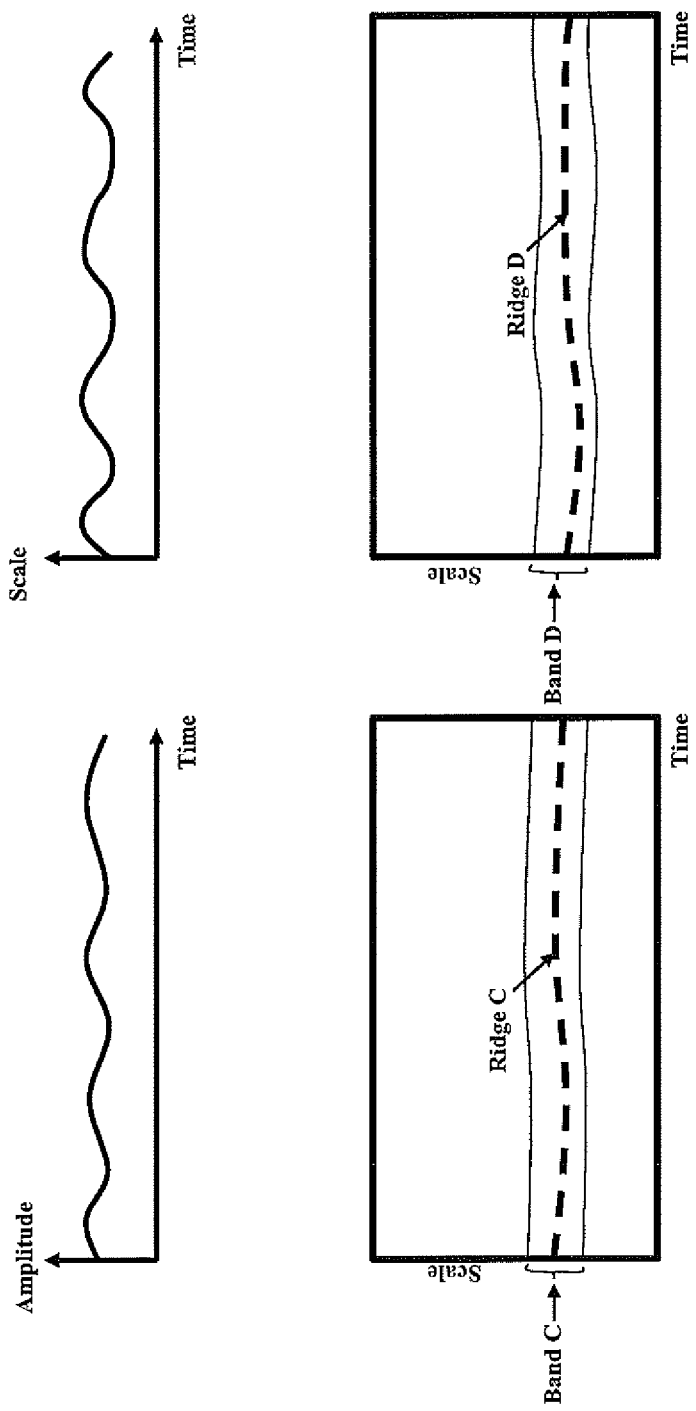
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_{0}^{\infty} T(a,b) \frac{1}{\sqrt{a}} \psi\left(\frac{t-b}{a}\right) \frac{da\,db}{a^2} \tag{15}$$

which may also be written as:

$$x(t) = \frac{1}{C_g} \int_{-\infty}^{\infty} \int_{0}^{\infty} T(a,b) \psi_{a,b}(t) \frac{da\,db}{a^2} \tag{16}$$

where $C_g$ is a scalar value known as the admissibility constant. It is wavelet type dependent and may be calculated from:

$$C_g = \int_{0}^{\infty} \frac{|\hat{\psi}(f)|^2}{f} df \tag{17}$$

Figure 3E:
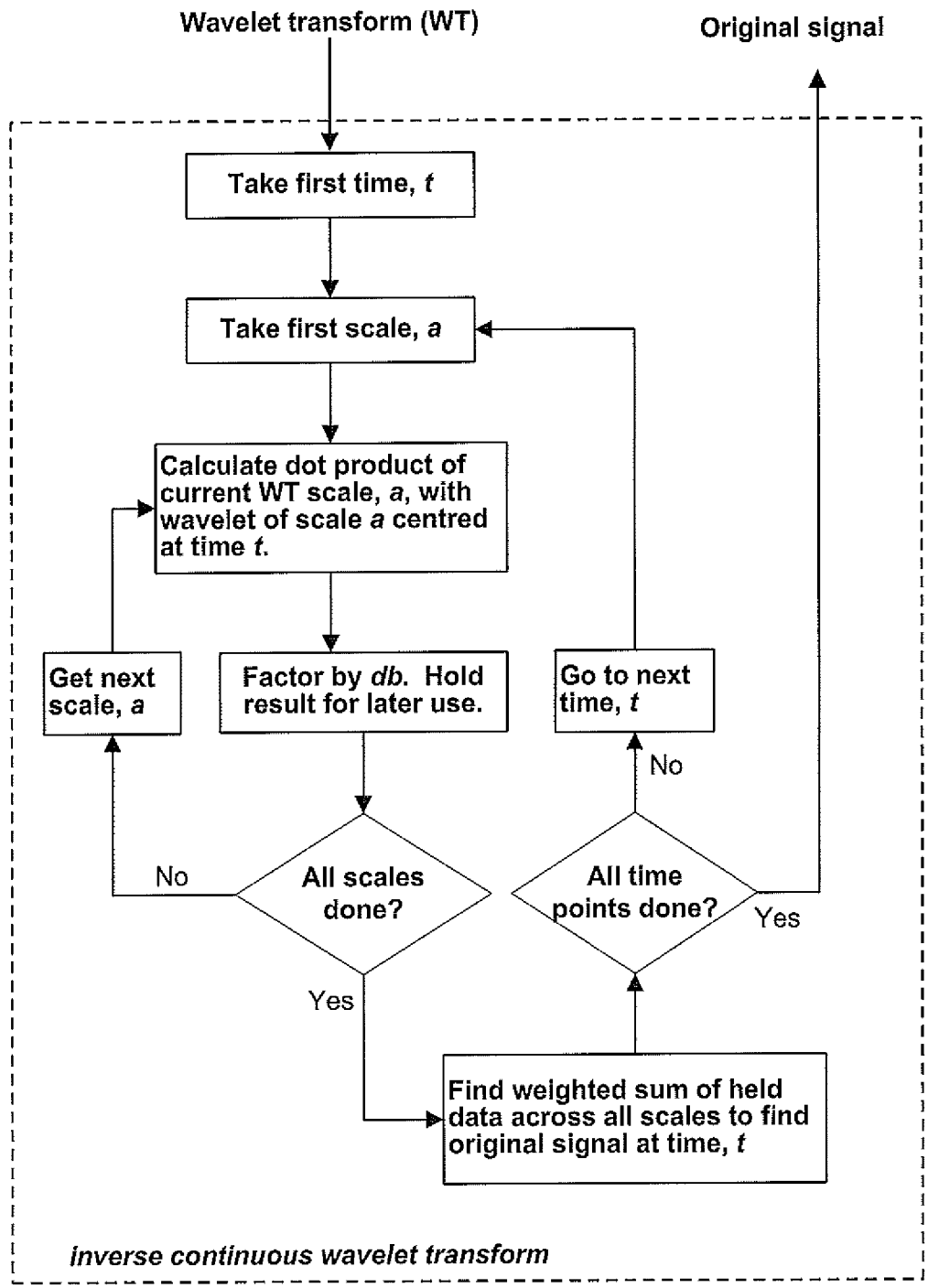
FIGS. 3(e) and 3(f) are flow charts of illustrative steps involved in performing an inverse continuous wavelet transform in accordance with embodiments.
Figure 3F:
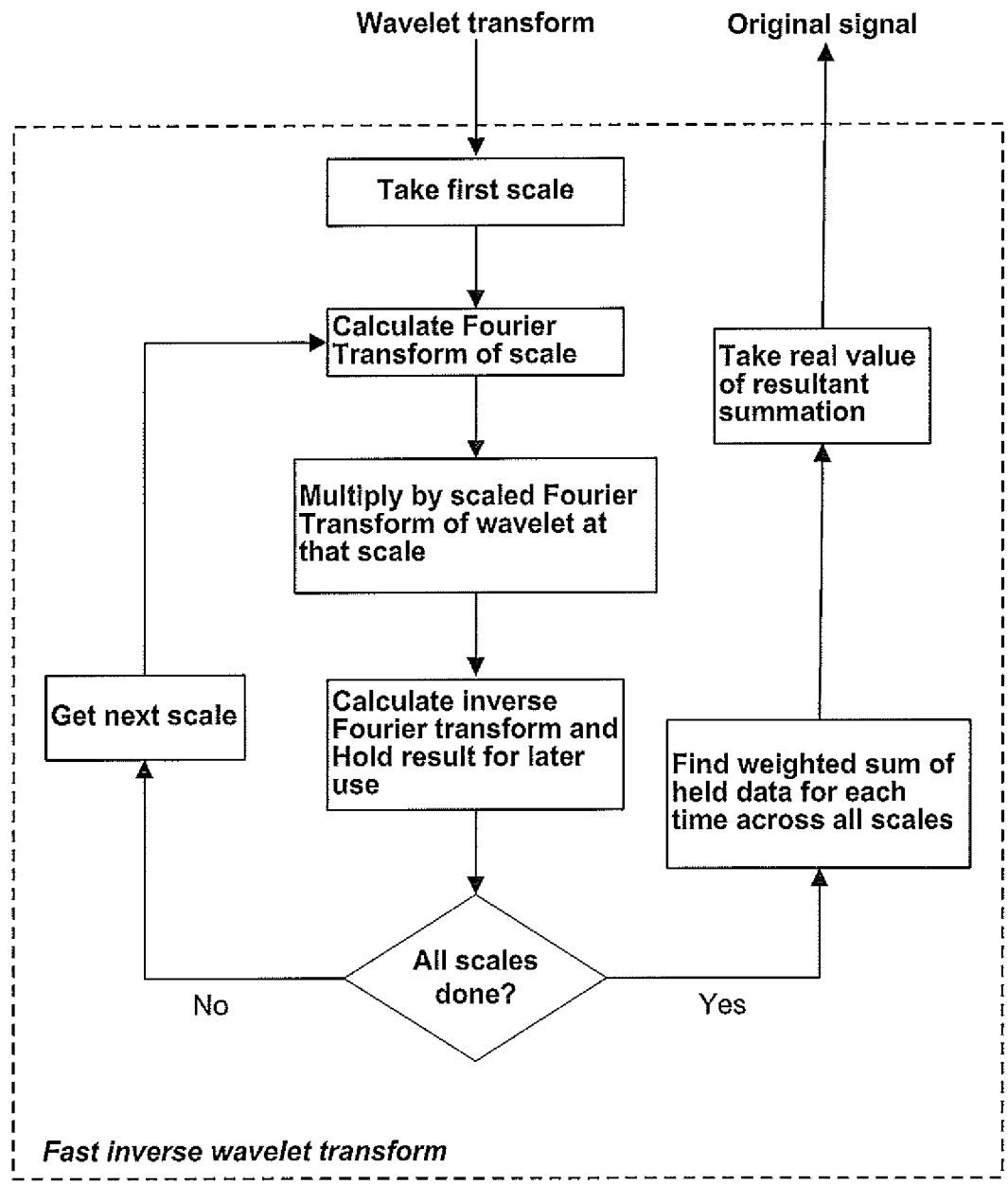

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
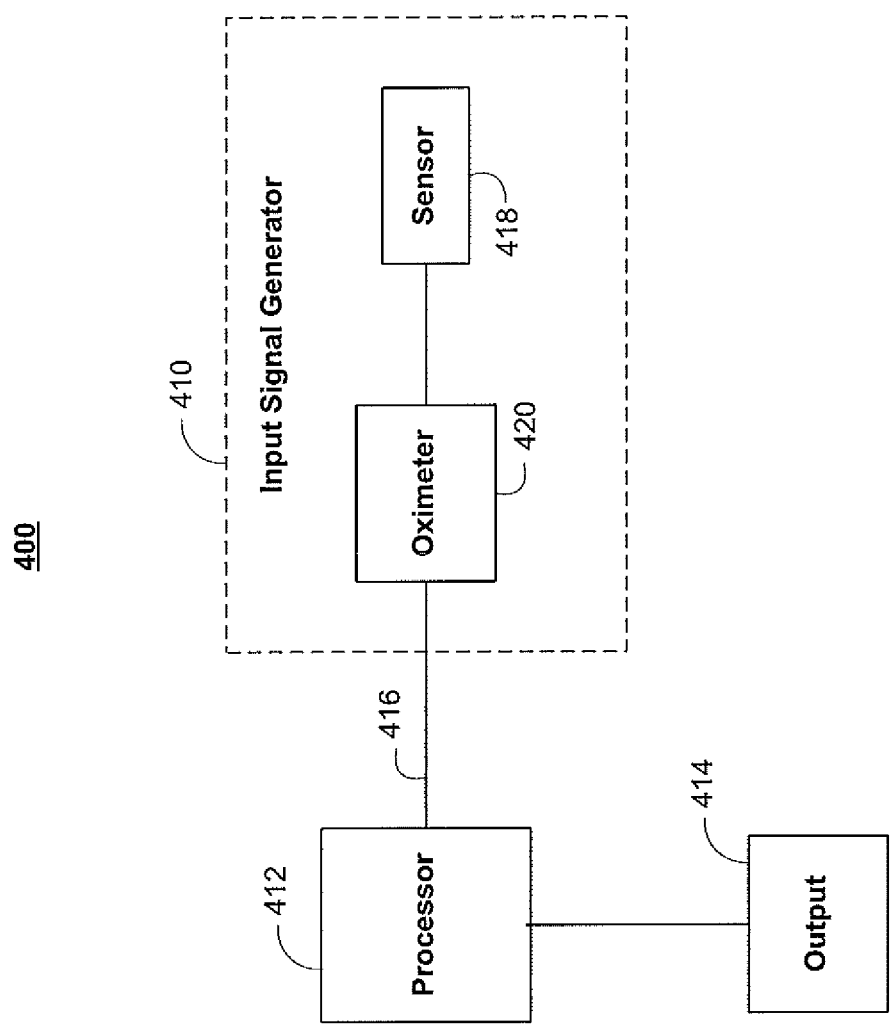
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms or signal processing of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, output 414 may form part of sensor 418 and may be connected to processor 412 via an output signal path. Output 414 may include, for example, a visible light emitter capable of indicating that a physiological parameter is being monitored using sensor 418 and processor 412. In response to receiving an output signal from processor 412, output 414 may emit light of any suitably visible color, the color being associated with a particular physiological parameter being monitored by system 400. Alternatively, output 414 may be signaled by processor 412 to emit visibly flashing light to indicate that the particular physiological parameter associated with the color has reached a critical threshold, or to indicate that sensor 418 is not successfully detecting the input signal 416 needed to monitor the physiological parameter. In some embodiments, output 414 may be signaled by processor 412 to emit visibly flashing light at a rate that corresponds to the rate of any suitable physiological parameter, such as a patient's respiration rate. If the rate of the physiological parameter reaches a clinically important threshold, output 414 may emit visibly flashing light at a different rate (e.g., at an increased rate) to visually alert a user of system 400 of the threshold being reached. It will be understood that output 414 may emit visibly flashing light at any suitable rate to alert a user of system 400 to a change in any suitable physiological parameter (e.g., a change in a patient's blood oxygen saturation level), and not just physiological parameters with an inherent rate.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Various approaches have been used for monitoring the blood pressure of living subjects. One approach is to insert a pressure sensor directly into a suitable artery of the subject. The sensor may be connected to a suitable monitoring device by a lead which passes through the subject's skin. This approach may provide highly accurate and instantaneous blood pressure measurements, but is very invasive. A surgical procedure is generally required to introduce the pressure sensor, and the fistula through which the lead exits the subject's body can provide a pathway for infection.

Another approach to measuring blood pressure uses a sphygmomanometer. A typical sphygmomanometer has an occluding cuff capable of being wrapped around a subject's arm. A pump is used to inflate the cuff, and an aneroid or mercury gravity sphygmomanometer is used to measure the pressure in the cuff. Such devices are widely used in hospitals, but are not well adapted for providing continuous blood pressure monitoring.

Some continuous non-invasive blood pressure monitoring (CNIBP) techniques have been developed that involve the use of two probes or sensors positioned at two different locations on a subject's body. The elapsed time, T, between the arrival of corresponding points of a pulse signal at the two locations may then be determined using the two probes or sensors. The estimated blood pressure, p, may then be related to the elapsed time, T, by $$p=a+b\cdot\ln(T) \quad (9)$$

where a and b are constants that are dependent upon the nature of the subject and the signal detecting devices. Other blood pressure equations using elapsed time may also be used. These techniques may be referred to as differential pulse transit time (DPTT)-based CNIBP.

In some embodiments, the constants a and b in equation (9) may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

The calibration may include performing calculations mathematically equivalent to $$a = c_1 + \frac{c_2(P_0 - c_1)}{\ln(T_0) + c_2} \quad (10)$$

and $$b = \frac{P_0 - c_1}{\ln(T_0) + c_2} \quad (11)$$

to obtain values for the constants a and b, where $c_1$ and $c_2$ are predetermined constants.

In other embodiments, determining the plurality of constant parameters in the multi-parameter equation (1) may include performing calculations mathematically equivalent to $$a=P_0-(c_3T_0+c_4)\ln(T_0) \quad (12)$$

and $$b=c_3T_0+c_4 \quad (13)$$

where a and b are first and second parameters and $c_3$ and $c_4$ are predetermined constants.

In some embodiments, the multi-parameter equation (9) includes a non-linear function which is monotonically decreasing and concave upward in a manner specified by the constant parameters.

Continuous and non-invasive blood pressure monitoring using these techniques is described in Chen et al. U.S. Pat. No. 6,566,251, which is hereby incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body.

The use of multiple probes or sensors in non-invasive continuous blood pressure monitoring provides reliable results. However, in some instances, the use of multiple separate probes or sensors at different locations on the subject's body may be cumbersome, especially for a mobile subject. Moreover, one of the multiple probes or sensors may become detached from the subject, resulting in a disruption in the continuous monitoring of the patient's blood pressure. Accordingly, some techniques for continuously monitoring a subject's blood pressure use only a single probe or sensor. In some embodiments, the single probe or sensor may detect a photoplethysmograph (PPG) signal generated, for example, by a pulse oximeter with an IR emitter. The PPG signal may then be analyzed and used to compute a time difference between two or more characteristic points in the PPG signal. The sensor also may use emitter 16 to emit light of any suitably visible color (e.g., orange) to indicate that the sensor is capable of being used as part of a patient's blood pressure monitoring. From this time difference, reliable and accurate blood pressure measurements may be computed on a continuous or periodic basis. This measurement technique is described in more detail in U.S. patent application Ser. No. 12/242,238, filed Sep. 30, 2008, entitled "SYSTEMS AND METHODS FOR NON-INVASIVE BLOOD PRESSURE MONITORING," which is incorporated by reference herein in its entirety.

In some embodiments, blood pressure measurements may be determined based on pulses in a PPG signal detected by a single sensor, for example, by measuring the area under a pulse or a portion of the pulse in the PPG signal. This technique is described in more detail in U.S. patent application Ser. No. 12/242,867, filed Sep. 30, 2008, entitled "SYSTEMS AND METHODS FOR NON-INVASIVE CONTINUOUS BLOOD PRESSURE DETERMINATION," which is incorporated by reference herein in its entirety.

In some embodiments, blood pressure measurements and blood oxygen saturation measurements may be made with the help of a combined sensor. This technique is described in more detail in U.S. patent application Ser. No. 12/242, 446, filed Sep. 30, 2008 entitled "SYSTEMS AND METHODS FOR COMBINED PULSE OXIMETRY AND BLOOD PRESSURE MEASUREMENT," which is incorporated by reference herein in its entirety.

For respiration effort measurements, emitter 16 may emit an IR wavelength that is detected by detector 18 after passing through patient tissue. The resulting PPG signal may be transformed (e.g., using a wavelet transform) into any suitable domain and may be represented as a spectrogram or scalogram (e.g., the energy density function of the wavelet transform, or any other suitable form of rescaling). Selected features of the scalogram may be analyzed to determine respiration effort. For example, the amplitude or energy of a time-scale band appearing on the scalogram may be indicative of a patient's breathing effort when the time-scale band is the patients breathing band. This technique is described in more detail in U.S. patent application Ser. No. 12/245,366, filed Oct. 3, 2008, entitled "SYSTEMS AND METHODS FOR DETERMINING EFFORT," which is incorporated by reference herein in its entirety.

Emitter 16 may emit an IR wavelength that is detected by detector 18 after passing through patient tissue. The resulting PPG signal may be used (e.g., by system 10) to obtain information about a patients respiration rate. For example, a portion of the PPG signal (e.g., an upstroke of the PPG signal) obtained from the patient may be selected. The portion may be mirrored about a desired vertical axis to create a pulse that includes the original signal portion and a new portion that mirrors the original selected portion. This technique may be repeated for another, different portion of the PPG signal (e.g., a downstroke) to create a second pulse. The first and second pulses that have been created through the mirroring technique may be combined to create a new signal. The new signal may be transformed in any suitable manner, including for example, by using a wavelet transform. A scalogram may be generated based at least in part on the transformed signal. From the scalogram, a time-scale band may be identified from which further information (e.g., ridge information or off-ridge information, where ridges may include the locus of points of local maxima in the time-scale plane) may be extracted. Further transformation of the information may create a second transformed signal that may also be used to generate a second scalogram. From the second scalogram, a region may be analyzed to determine the patient's respiration rate. This technique is described in more detail in U.S. Provisional Patent Application No. 61/077,062, filed Jun. 30, 2008, entitled "DERIVING PHYSIOLOGICAL PARAMETERS FROM PLETHYSMOGRAPH BY MIRRORING UPSTROKE OR DOWNSTROKE," which is incorporated by reference herein in its entirety.

The present disclosure relates to patient monitoring, and more particularly, relates to a sensor that provides color-coded indications that various physiological parameters are being monitored, such as blood oxygen saturation, blood pressure, respiration rate, and respiration effort. By "color-coded," it is meant that a sensor that emits a particular visible color may be used in association with monitoring a particular physiological parameter. For example, a sensor that emits light of an orange color or includes orange components may be used in association with monitoring a patients blood pressure because the color orange may be color-coded to represent the physiological parameter of blood pressure. Similarly, a sensor that emits light of a green color or includes green components (e.g., a green sensor housing, a green sensor lead) may be used in association with monitoring a patient's respiration rate because the color green has been color-coded to represent the physiological parameter of respiration rate. A sensor that emits light of a red color may be used in association with monitoring blood oxygen saturation, as the visible RED wavelength emitted by emitter 16 may also be used to sense a physical characteristic that is used to monitor the physiological parameter. In some embodiments, the sensor may emit more than one color (e.g., red and blue) in association with sensing a first and/or a second physical characteristic and monitoring one or more physiological parameters. The visible combination of the colors (e.g., purple) may be color-coded to represent the monitoring of more than one physiological parameter (e.g., blood oxygen saturation and blood pressure).

Figure 5:
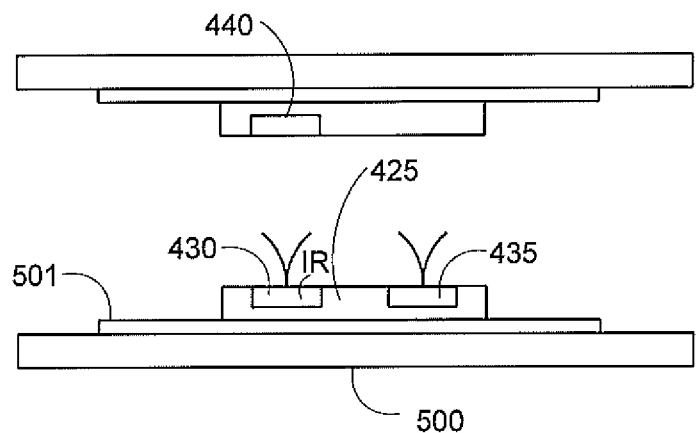
FIG. 5 shows an illustrative cross-section of a sensor in accordance with some embodiments.
Figure 6:
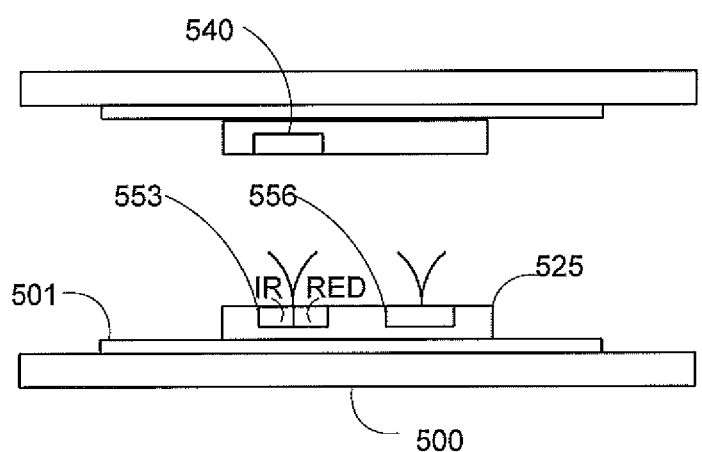
FIG. 6 shows an illustrative cross-section of a sensor in accordance with some embodiments.

FIGS. 5-6 show an illustrative cross-section of sensors in accordance with the present disclosure. The sensors in FIGS. 5-6 may include any suitable sensors (including, but not limited to, pulse oximeters) used to sense at least one physical characteristic of a patient to which the sensor is connected. For example, the sensors in FIGS. 5-6 may be used to sense a physical characteristic associated with monitoring physiological parameters such as a patient's blood oxygen saturation level, blood pressure, respiration rate, or respiration effort. In some embodiments, the sensors in FIGS. 5-6 may additionally include any other components associated with monitoring any other suitable physiological parameters (e.g., the electrical activity of a patient's heart).

FIG. 5 shows an illustrative cross-section of sensor 425 containing a single wavelength emitter 430 and detector 440 for sensing a physical characteristic (e.g., pulsatility of the blood in the arteries of a patient to which sensor 425 may be attached) that may be used in monitoring a physiological parameter, and a visible light emitter 435. Sensor 425 may be positioned in any suitable location on a patient (e.g., finger, head, foot) to sufficiently sense a physical characteristic. Emitter 430, detector 440, and visible light emitter 435 may be secured to support structure 500 using adhesive 501 or any other suitable attachment technique. Further, while adhesive 501 is shown as securing the underside of sensor components 430 and 435 to support structure 500, it should be understood that sensor components 430 and 435 may be secured over support structure 500 (as shown), under support structure 500, or at least partially embedded in support structure 500. Similarly, adhesive 501 or an equivalent attachment medium may be located under the sensor components (as shown), around the sensor components, over the sensor components (as shown with detector 440), or some combination thereof. In some embodiments, one or more of the sensor components may be integrated with or built directly onto support structure 500. Support structure 500 may be made of any material or combination of materials suitable for disposable and reusable probes. Support structure 500 may be made of a flexible material that allows sensor components 430 and 435 to achieve close contact with desired sensor site locations, even when those locations are across a curved surface such as a patient's head.

In some embodiments, the wavelength of emitter 430 may be an IR wavelength that is flashed at an imperceptibly high frequency to sense a physical characteristic. The sensed physical characteristic may be used to monitor a physiological parameter, such as the patient's blood pressure, respiration rate or respiration effort. The emitter-detector separation and wavelength selection of emitter 430 may be optimized for sensing this physical characteristic.

Since IR light is not perceptible to a user of sensor 425, a user may not perceive whether sensor 425 is working or what physiological parameters can be monitored in association with attaching sensor 425 to a patient by just looking at sensor 425. Visible light emitter 435 may emit any suitable visibly colored light (e.g., may flash visibly colored light intermittently with the light emitted by the IR emitter 430 so as not to interfere with the sensing of a physical characteristic, but at an imperceptibly high frequency that makes the light appear constant) to indicate to a user of sensor 425 that sensor 425 may be used in association with monitoring a particular physiological parameter(s). For example, if emitter 430 and detector 440 are used to sense a physical characteristic (e.g., the pulsatility of the blood in a patient's arteries), which in turn may permit the patients blood pressure to be monitored, visible light emitter 435 may emit orange light to indicate to a user that sensor 425 is intended for use with monitoring blood pressure through a CNIBP approach. The visible light emitted by visible light emitter 435 is not used by sensor 425 to sense a physical characteristic. In some embodiments, visible light emitter 435 may be at a distance from IR emitter 430 (e.g., visible light emitter 435 may be positioned outside of sensor 425) such that visible light emitter 435 may not be required to flash intermittently with IR emitter 430 so as to not to interfere with the sensing of a physical characteristic. For example, visible light emitter 435 may be positioned, either on one of the leads or connectors of sensor 425 (e.g., cable 24) or on a monitor socket that connects sensor 425 to a monitor (e.g., the socket that connects cable 24 to monitor 14), such that visible light emitter 435 is sufficiently remote from IR emitter 430 to permit visible light emitter 435 to flash at any suitable frequency that appears visibly constant without interfering with the sensing role of IR emitter 430.

Any physiological parameter that may be monitored using a physical characteristic sensed by sensor 425 may have a unique color associated with it (e.g., the sensor may be color-coded to indicate its association with monitoring a particular physiological parameter). For example, if sensor 425 is sensing a physical characteristic that is used to monitor the patient's respiration rate, visible light emitter 435 may flash green light at a high enough frequency to appear constant to a user of sensor 425. If sensor 425 is sensing a physical characteristic that is used to monitor the patient's respiration effort, visible light emitter 435 may flash yellow light interspersed with the flashing of IR light from emitter 430 so that the yellow light appears constant to a user of sensor 425. Sensor 425 may include a different visible light emitter 435 for each different physiological parameter. It is to be understood that sensor 425 could also be depicted in FIG. 5 as though visible light emitter 435 were a part of component 430, but nonetheless the light emitted by visible light emitter 435 may not be used to sense a physical characteristic.

Color-coding sensor 425 may be useful as it avoids sensor 425 from being used in the wrong clinical application and alerts the user to the purpose for which sensor 425 is also attached to the patient. For example, color-coding sensor 425 to emit visible light of a particular color associated with a particular physiological parameter (e.g., emitting orange light when CNIBP is being monitored) may prevent a user from using sensor 425 when the patient's blood oxygen saturation levels need to be monitored and the user should be using a sensor that emits red light instead. The color-coding of sensor 425 may also extend further in some embodiments, as the housing of sensor 425, the lead or the connector used to attach sensor 425 to a monitor, and/or the monitor socket into which sensor 425 connects may be of the same color as the light emitted by visible light emitter 435. In those instances in which only IR light may be needed to sense a physical characteristic, the addition of visible light emitter 435 also may serve the purpose of visibly indicating to the user that sensor 425 is functioning.

In some embodiments, visible light emitter 435 may flash light on an increased cycle time (e.g., visible light emitter 435 may be switched to OFF for a prolonged period of time, such as 0.5 seconds, then may cycle at a high frequency with the IR light as described above, and then may repeat this sequence), thereby making the flashing of the colored light visible to a user of sensor 425. A visible flashing of the colored light may be used for safety purposes, by indicating to the user that sensor 425 has sensed a threshold in a physical characteristic, and that a potentially dangerous physiological state has been reached or an important change involving sensor 425 has occurred. For example, sensor 425 may be used to sense a physical characteristic (e.g., the pulsatility of the blood in a patient's arteries) as part of monitoring the patient's blood pressure. Visible light emitter 435 may emit visibly flashing orange light to notify a user that the patient's status has changed (e.g., pulsatility has markedly increased or decreased, which may signify a marked change in the patient's blood pressure). In some embodiments, visible light emitter 435 may emit light of a different visible color to indicate a change in patient status. In some embodiments, visible light emitter 435 may emit light that flashes in sync with a natural body cycle of the patient (e.g., the patient's heart rate) or in sync with a physiological parameter (e.g., the patient's respiration rate) to provide an additional visual cue as to the patient's status.

Alternatively, visible light emitter 435 may emit visibly flashing light to notify a user that sensor 425 has sensed a change in the quality of a physical characteristic it is sensing (e.g., because sensor 425 has been affected by excessive patient movement or a low signal-to-noise ratio, or because sensor 425 has been disconnected from the patient). In some embodiments, visible light emitter 435 also may emit visibly flashing light to indicate that it is now associated with sensing a second physical characteristic or is associated with monitoring a new or different physiological parameter. In some embodiments, visible light emitter 435 also may emit visibly flashing light in a unique pattern to alert a user of sensor 425 that sensor 425 has exceeded its operational lifespan and should be replaced by a new sensor 425.

In some embodiments, the period of time during which visible light emitter 435 is switched OFF may also be altered to indicate a change in the patients status. For example, if visible light emitter 435 emits orange light that appears to flash slowly, a user may be alerted that the patient's blood pressure, for example, has reached a dangerous threshold. If visible light emitter 435 visibly flashes orange light at an increasing rate, this increase may indicate to the user that the patient's status is worsening or has reached a point at which user intervention is required.

In some embodiments, if visible light emitter 435 is not being used to indicate that a physiological parameter of the patient is being monitored, visible light emitter 435 can be used to indicate only when a change in patient status occurs or when a problem otherwise arises. For example, visible light emitter 435 may remain in the OFF state until a change in patient status is sensed. Once a threshold is sensed, visible light emitter 435 may then begin emitting light in an ON-OFF pattern, interspersed with the flashing of the IR light of emitter 430, at a frequency perceptible to the user as flashing.

FIG. 6 shows an illustrative cross-section of sensor 525 containing a dual wavelength emitter 553 and detector 540 for sensing at least one physical characteristic, and a visible light emitter 556. It is to be understood that sensor 525 could also be depicted in FIG. 6 as though visible light emitter 556 were a part of component 553, but nonetheless the light emitted by visible light emitter 556 may not be used to sense a physical characteristic. Sensor 525 may be coupled to support structure 500 using adhesive 501. Dual-wavelength emitter 553 may emit red and IR wavelengths that may be used to sense a physical characteristic (e.g., light attenuation through a patient's tissue) at more than one wavelength or a first physical characteristic and a second physical characteristic. The emitter-detector separation and wavelength selection of emitter 553 may be optimized for sensing a physical characteristic. The red wavelength emitted by emitter 553 is also visible to a user of sensor 525. In some embodiments, the red wavelength emitted by emitter 553, or the visible combination of the red wavelength and the visible light emitted by visible light emitter 556, may be used in connection with indicating the monitoring of a particular physiological parameter (e.g., blood oxygen saturation) associated with a physical characteristic or characteristics sensed by sensor 525. At the same time, because emitter 553 is capable of sensing a physical characteristic using the IR wavelength, sensor 525 may be used in connection with monitoring a second physiological parameter (e.g., blood pressure) and visible light emitter 556 may emit light of a particular color (e.g., orange) to color-code sensor 525 for use with monitoring the patient's blood pressure. To avoid user confusion over the capabilities of sensor 525, visible light emitter 556 may not emit the same visible red wavelength emitted by emitter 553.

In some embodiments, if sensor 525 is actively sensing at least one physical characteristic that may be used in connection with monitoring more than one physiological parameter, both the red wavelength within emitter 553 and the colored light emitted by visible light emitter 556 may appear to a user as visibly combined. If, for example, emitter 553 emits red and IR light to sense a physical characteristic or characteristics that is used to monitor blood oxygen saturation, and emitter 553 emits IR light to sense a physical characteristic used in monitoring blood pressure, respiration rate, and/or respiration effort, thereby causing visible light emitter 556 to emit blue light, then sensor 525 may appear to be emitting purple light to a user from the visible combination of the blue and red wavelengths. If sensor 525 reverts to sensing a physical characteristic for use with monitoring one physiological parameter (e.g., blood oxygen saturation), visible light emitter 556 may stop emitting light and sensor 525 may appear red to a user. In either instance, visible light emitter 556 is not used to sense a physical characteristic.

In some embodiments, more than one visible light emitter 556 may be included in sensor 525, if sensor 525 may be used in association with monitoring more than two physiological parameters. In some embodiments, visible light emitter 556 may emit visible light that cycles with the red and IR wavelengths of emitter 553 to indicate a change in the patients status or a change in the signal quality (e.g., a change in the quality of a physical characteristic or characteristics being sensed by sensor 525). For example, a low signal-to-noise ratio condition in which sensor 525 is not adequately sensing a physical characteristic could trigger the cycling of visible light emitter 556 together with the red and IR wavelengths emitted by emitter 553 to make sensor 525 appear to change color. This low signal-to-noise condition could indicate that sensor 525 may not be properly attached to a patient (e.g., attached to an area of low perfusion). As with visible light emitter 435, visible light emitter 556 may be at a distance from emitter 553 (e.g., visible light emitter 556 may be positioned outside of sensor 525) such that visible light emitter 556 may not be required to emit visible light that cycles with the red and IR wavelengths of emitter 553 so as to not to interfere with the sensing of a physical characteristic.

In some embodiments, a change in color of sensor 525 or a visible flashing of colored light from visible light emitter 556 could indicate that sensor 525 is being used in connection with monitoring more than one physiological parameter. For example, using sensor 525 to sense a physical characteristic or characteristics associated with monitoring both blood pressure and respiration rate could be indicated by visible light emitter 556 emitting green light. Alternatively, using sensor 525 to sense a physical characteristic or characteristics associated with monitoring blood pressure and blood oxygen saturation could be indicated by visible light emitter 556 emitting blue light that, when flashed in sequence with the red wavelength of emitter 553 as described above, may appear combined as purple to a user of sensor 525.

In some embodiments, where sensor 525 is associated with the monitoring of more than one physiological parameter, visible light emitter 556 and the red wavelength in emitter 553 may visibly flash independently of each other to provide independent information about the status of more than one physiological parameter. For example, if sensor 525 has sensed a threshold in a physical characteristic that would be associated with a threshold in the patient's blood pressure, but a threshold in a physical characteristic associated with monitoring the patient's blood oxygen saturation has not been sensed, then visible light emitter 556 may visibly flash blue light, but the red wavelength in emitter 553 may not appear to flash to a user. In situations where a threshold in the patient's status has been sensed with respect to both physiological parameters, both the red wavelength and the blue wavelength may appear combined as purple light to a user and the purple light may appear to flash to a user. As with sensor 425, visible light emitter 556 and/or emitter 553 may emit visibly flashing light in a unique pattern to alert a user of sensor 525 that sensor 525 has exceeded its operational lifespan and should be replaced by a new sensor 525.

In addition to situations where a threshold in the patient's status has been sensed with respect to both physiological parameters, a flashing of the combined visible wavelengths from emitter 553 and visible light emitter 556 may be used to indicate other status changes. For example, if sensor 525 has become detached from a patient, is sensing excessive noise along with a physical characteristic or characteristics, or is otherwise sensing a low signal to noise ratio, both the red wavelength and the blue wavelength emitted from emitters 553 and 556, respectively, may appear combined as purple light to a user and the purple light may visibly flash.

In some embodiments, instead of being positioned in sensor 525 or 425, visible light emitter 556 (or visible light emitter 435) may be positioned on the lead or the connector used to attach sensor 525 or 425 to a monitor. Alternatively, visible light emitter 556 or 435 may be positioned on the monitor socket into which sensor 525 or 425 connects, or on any other suitable surface to provide to a user of sensor 525 or 425 a visual indication of what physiological parameter(s) is being monitored and the status therein. In some embodiments, sensor 525 may be a finger clip for attachment to a patients finger. For example, sensor 525 may house emitter 553 for emitting red and IR wavelengths to sense a physical characteristic or characteristics associated with monitoring the patient's blood oxygen saturation and the patient's blood pressure. Outside of the housing, such as on the exterior of the finger clip, on the lead, or on the monitor socket, another visible light source may emit a visible light (e.g., orange or blue) that is color-coded to indicate that sensor 525 may be used in association with monitoring blood oxygen saturation and blood pressure. In some embodiments, an array of visible light sources may be positioned outside of the housing and each visible light source may independently emit visible light that is color-coded to indicate that sensor 525 is being used in association with monitoring a particular physiological parameter. For example, red light may be emitted by one visible light source outside of the housing to indicate that blood oxygen saturation is being monitored, orange light may be emitted by a second visible light source outside of the housing to indicate that blood pressure is being monitored, blue light may be emitted by a third visible light source outside of the housing to indicate that respiration rate is being monitored, and green light may be emitted by a fourth visible light outside of the housing source to indicate that respiration effort is being monitored. It will be understood that these four visible light sources, external to the finger clip and emitter 553, are not being used to sense a physical characteristic or characteristics related to the particular physiological parameter(s) being monitored. Alternatively, the red light being emitted to indicate that blood oxygen saturation is being monitored may originate from the red wavelength of emitter 553 and not from a light source external to sensor 525. In that situation, only three independent visible light sources may be positioned externally on the finger clip.

In some embodiments, sensor 425 or 525 may additionally include any other necessary components (e.g., an electrode) associated with monitoring any other suitable physiological parameters (e.g., the electrical activity of a patient's heart). In such situations, visible light emitter 435 or 556 may still be used to indicate to a user of sensor 425 or 525 that particular physiological parameters are being monitored. For example, emitter 553 may sense a physical characteristic or characteristics associated with monitoring the patients blood oxygen saturation level. The red wavelength emitted by emitter 553 may be visible to a user of sensor 525 and may indicate that blood oxygen saturation is being monitored. Concurrently, sensor 525 may include an electrode sensing signals useful in constructing an electrocardiogram, or a recording used to monitor the electrical activity of the patient's heart. Visible light emitter 556 may emit blue light to indicate to a user of sensor 525 that the electrical activity of the patient's heart is being monitored. Together, the red and blue light may combine to appear purple to a user of sensor 525 to indicate the monitoring of both physiological parameters. As described above, one or both of the visible light emitters also may emit visibly flashing light to indicate a change in status of one or both of the physiological parameters being monitored or a change in the status of sensor 525.

In some embodiments, visible light emitter 556 and/or the red wavelength emitter within emitter 553 may be replaced by another emitter that may be used to sense a physical characteristic or characteristics, but may not emit a visible light in doing so. Alternatively, the red wavelength emitter within emitter 553 may be used to sense a physical characteristic or characteristics and may emit light of a visible color, although visible light emitter 556 may emit light of a different visible color than the light emitted by the red wavelength emitter. In some embodiments, visible light emitter 556 and/or the red wavelength emitter may emit light of a visible color, but may not be used to sense a physical characteristic.

Figure 7:
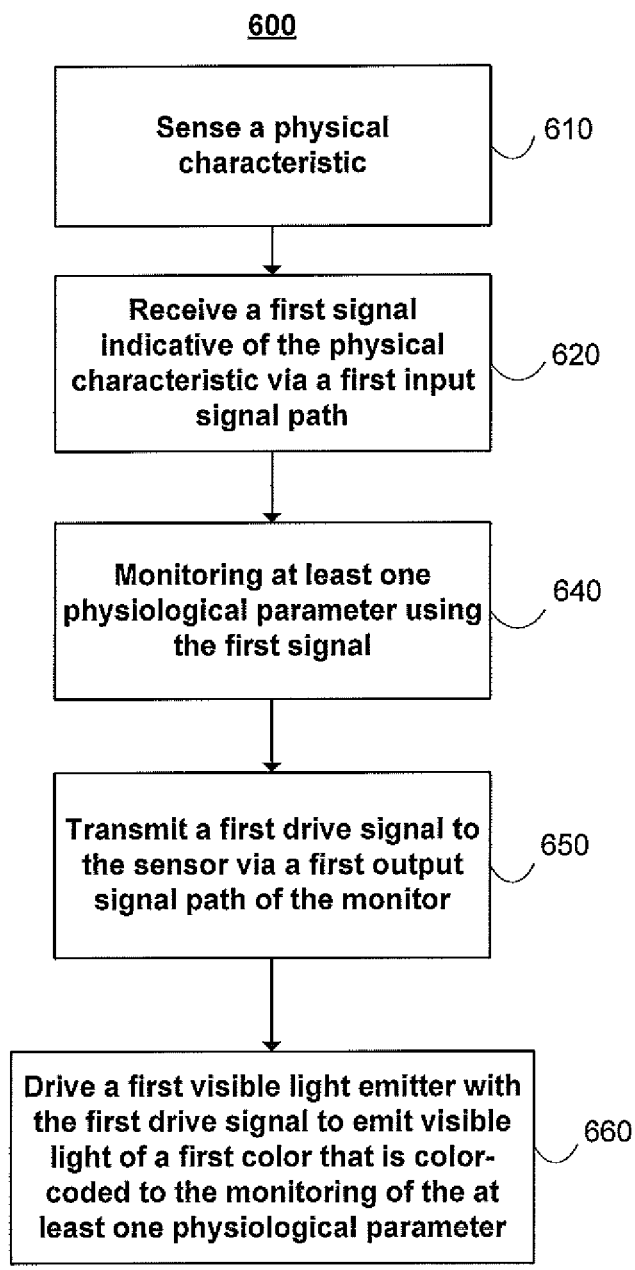
FIG. 7 illustrates a process performed in accordance with some embodiments.

FIG. 7 illustrates a process performed in accordance with some embodiments. Process 600 may begin at step 610 as a physical characteristic (e.g., pulsatility of the blood in the patients arteries) may be sensed using a sensor such as sensor 425 or 525. The physical characteristic may be sensed using an infrared light emitter and a detector. At step 620, a first signal that may be indicative of the physical characteristic sensed at step 610 may be received by a monitor (e.g., monitor 14) using a first input signal path. At step 640, the first signal is used by a processor (e.g. processor 48) to monitor at least one physiological parameter with which the physical characteristic is associated (e.g., blood pressure). At step 650, a first drive signal that results from the processor monitoring the physiological parameter is transmitted via an output signal path from the monitor to the sensor.

At step 660, the first drive signal drives a visible light emitter within the sensor and not used to sense the physical characteristic (e.g., visible light emitter 435 or 556) to emit visible light of a color that is color-coded to represent the monitoring of the particular physiological parameter. If the sensor at step 610 used more than one wavelength to sense the first physical characteristic and/or a second physical characteristic of a patient (e.g., using RED and IR wavelengths from emitter 553), then a second signal may be received at the monitor at step 620 via a second input signal path. The second signal may be used by the processor at step 640 to monitor a second physiological parameter (e.g., blood oxygen saturation), and a second drive signal may be transmitted to the sensor via a second output signal path to drive the visible light emitter that was used to sense the first physical characteristic and/or a second physical characteristic (e.g., the red emitter of emitter 553) to emit color-coded light associated with monitoring the second physiological parameter.

In some embodiments, a physical characteristic or characteristics associated with monitoring the second physiological parameter may be sensed by an infrared emitter and a second light emitter that does not emit visible light. The second physiological parameter may be monitored without requiring a second visible color (e.g., the red color from the red emitter) to appear. For example, the appearance of the visible light from visible light emitter 435 or 556 may indicate that both physiological parameters are being monitored by sensing a physical characteristic or characteristics. In some embodiments, a physical characteristic or characteristics associated with monitoring the second physiological parameter may be sensed by one or more infrared emitters, producing more than one signal to be received by the monitor, but a second visible light emitter still may be driven to emit visible light indicating that the second physiological parameter is being monitored.

Figure 8:
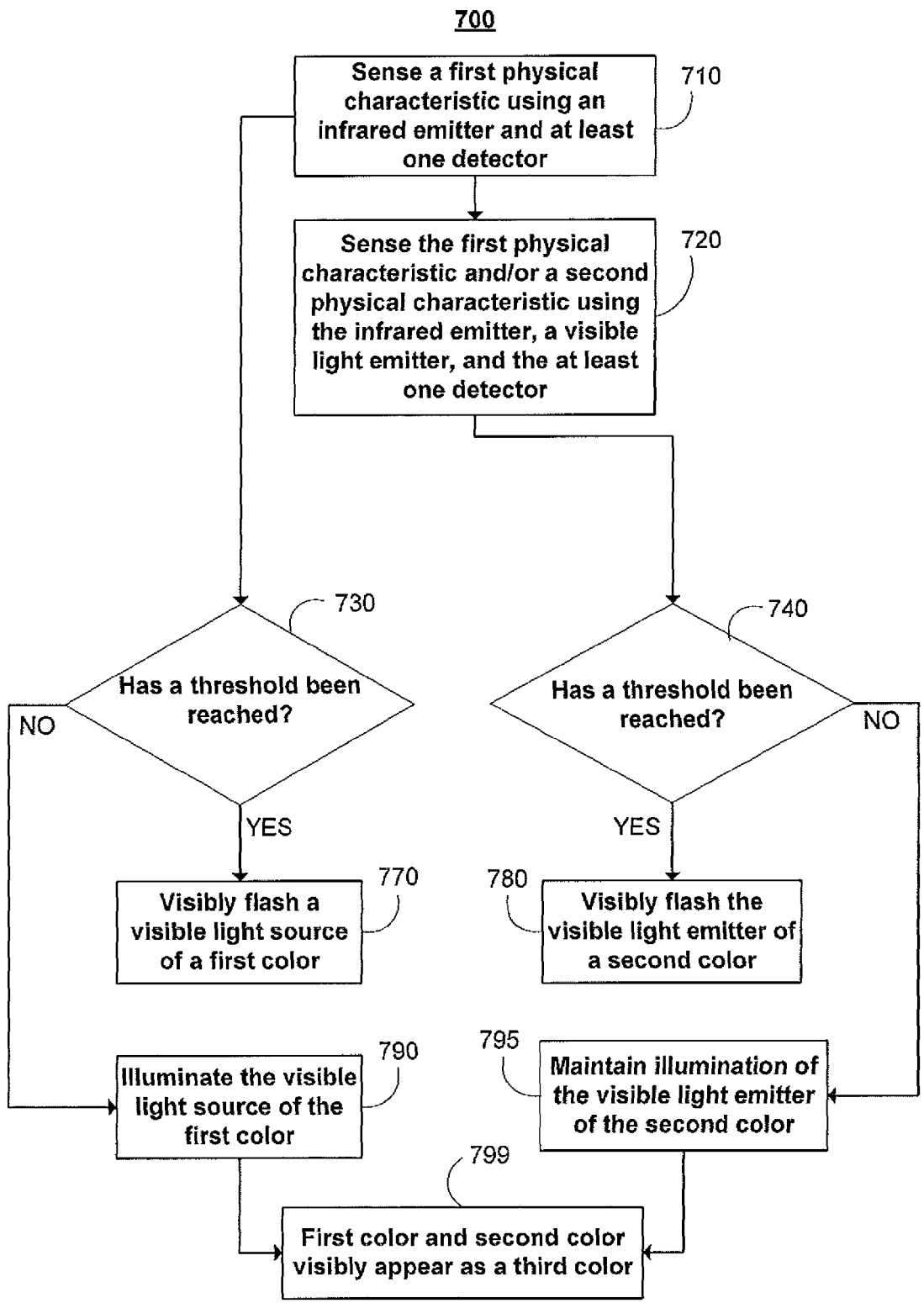
FIG. 8 illustrates a process performed in accordance with some embodiments.

FIG. 8 illustrates a process performed in accordance with some embodiments. Process 700 begins at step 710 where a first physical characteristic (e.g., pulsatility of the blood in the patient's arteries) may be sensed using an infrared light emitter and a detector from sensor 425 or 525. At step 720, the first physical characteristic and/or a second physical characteristic may be sensed by the sensor (e.g., sensor 525) using the infrared emitter, the detector and a visible light emitter that emits light of a particular color. The sensed physical characteristic(s) may be associated with any suitable physiological parameter or parameters, such as blood oxygen saturation, blood pressure, respiration rate, and/or respiration effort. In some embodiments, the first physical characteristic and/or a second physical characteristic may be sensed at step 720 by the infrared emitter, the detector, and a second light emitter that does not emit visible light. In some embodiments, steps 710 and 720 may be reversed.

At steps 730 and 740, respectively, the first physical characteristic and/or a second physical characteristic may be analyzed to determine whether a threshold value (e.g., a value indicating a change in the patient's status to a dangerous condition, or a value indicating a disconnection of the sensor or an excess of patient movement) has been sensed. If so, a visible light source (e.g., emitter 435, 556, or the red wavelength of emitter 553) may be used at steps 770 and 780, respectively, to emit visibly flashing light to alert a user of the sensor that a threshold has been attained. The light emitted by the visible light source at step 770 is of a first color that may indicate to a user what physical characteristic, and by extension what physiological parameter or parameters, has attained that threshold. The light emitted by the visible light emitter at step 780 (and, in some embodiments, used in step 720 to sense the first physical characteristic and/or a second physical characteristic) may be of a second color, different than the first color emitted in step 770. It is to be understood that step 770 is independent of step 780. The visible light source may visibly flash light at step 770 to indicate a threshold condition with respect to a physical characteristic without also requiring process 700 to advance to step 780 or requiring the visible light emitter of step 780 to visibly flash light.

If the first physical characteristic and/or a second physical characteristic sensed at steps 710 and 720 are analyzed and are determined not to be at a threshold level, then at steps 790 and 795, respectively, the visible light source may emit light of the first color and the visible light emitter may emit light of the second color. Both emissions may appear to be constant (although the light may be emitted at a rate imperceptible to the user and may be interspersed with the flashing of emitter 430 or emitter 553) and may be color-coded to represent the monitoring of one or more particular physiological parameters. This appearance of constant colored light may indicate to a user that the sensor is sensing a physical characteristic or characteristics associated with the color-coded physiological parameter or parameters, and that either the patient is not experiencing a dangerous condition or the sensor is not experiencing any difficulties or malfunctions.

If process 700 reaches both steps 790 and 795, then process 700 may advance to step 799, where the emission of the first color and the second color may visibly combine to produce a third color. For example, if the visible light source emits blue light at step 790 to indicate that the sensor is sensing the first physical characteristic associated with a first physiological parameter, and the visible light emitter emits red light at step 795 to indicate that the sensor is sensing the first physical characteristic and/or a second physical characteristic associated with the first physiological parameter and/or a second physiological parameter, then the emission of red and blue light together may appear as purple to a user of the sensor at step 799. This visibly combined light may indicate to the user that the sensor may be used in association with monitoring one or more physiological parameters. In some embodiments, if both the visible light source and the visible light emitter were emitting visibly flashing light at the same time and at the same frequency, then the visible flashing may appear as the third color and may indicate that a physical characteristic of one or more physiological parameters may have reached a threshold value. Alternatively, the visible light source may emit visibly flashing light at a rate or at a time different from the visibly flashing light of the visible light emitter, thereby permitting the flashing light to be perceived independently as the first and second colors.

If the second light emitter used in step 720 to sense the first physical characteristic and/or a second physical characteristic does not also emit visible light, then in some embodiments, the visible light emitter used in step 770 and 790 may be employed in any suitable fashion (e.g., may visibly flash in a distinctive pattern) at steps 780, 795, and 799 to indicate whether a threshold may have been reached at step 740. In some embodiments, at step 720, if the first physical characteristic and/or a second physical characteristic is sensed using an infrared emitter and a detector, but not a visible light emitter, then a visible light emitter may nonetheless be employed at steps 780, 795, and 799 to indicate whether or not a threshold has been reached with respect to monitoring the first physiological parameter and/or a second physiological parameter.

FIG. 9 illustrates a process performed in accordance with some embodiments. Process 800 begins at step 805 where a monitor (e.g., a multi-parameter monitor such as monitor 14) may determine whether a CNIBP signal has been received via a first input signal path, where the CNIBP signal may be indicative of a physical characteristic sensed by a sensor (e.g., sensor 525) that is capable of sensing a physical characteristic or characteristics associated with monitoring both CNIBP and blood oxygen saturation ($SpO_2$) as physiological parameters. In some embodiments, the signal and the sensor at step 805 may be related to monitoring another physiological parameter, such as respiration rate or respiration effort. If the CNIBP signal has not been received, process 800 may return to step 805 until a CNIBP signal is received at the monitor. If the CNIBP signal is received, process 800 may advance to step 807, where the monitor may determine whether a $SpO_2$ signal also has been received, and may also advance to step 811, where the CNIBP signal is monitored using a processor (e.g., processor 48) in the monitor. In some embodiments, step 807 may precede step 805. At step 807, the monitor may determine whether the $SpO_2$ signal has been received from first and second input signal paths, as the $SpO_2$ signal may be indicative of a physical characteristic or characteristics being sensed at the red and IR wavelengths. If the $SpO_2$ signal has not been received, process 800 may return to step 807 until an $SpO_2$ signal is received, although process 800 may also simultaneously proceed to step 811. If an $SpO_2$ signal has been received, process 800 may advance to step 814, where the $SpO_2$ signal is monitored using the processor within the monitor. It will be understood that, while steps 805 and 807 are depicted in FIG. 9 as decision steps performed by a monitor, in some embodiments the monitor will receive the CNIBP and $SpO_2$ signals at steps 805 and 807 without performing a determination as to whether the CNIBP and $SpO_2$ signals have been received.

At steps 811 and 814, the processor within the monitor may use the CNIBP and $SpO_2$ signals received from the input signal paths to calculate and monitor a patients blood pressure and blood oxygen saturation levels, respectively. For example, a patient's blood pressure and blood oxygen saturation level may be calculated and monitored by any of the methods described above. In some embodiments, previous signal values may be stored in the processor's memory (e.g., ROM 52 or RAM 54) for comparison with current values of the signals. In some embodiments, the physiological parameters may be displayed on display 20 in any suitable fashion or may be analyzed using user inputs 56.

At steps 815 and 818, the CNIBP and $SpO_2$ signals received in the processor may be analyzed to determine whether either signal has reached a threshold value. If so, process 800 may advance to steps 821 and 825 for the CNIBP parameter, and/or steps 822 and 826 for the $SpO_2$ parameter, respectively, where the processor may transmit a drive signal via the monitor's output signal path to drive a visible light emitter to emit visibly flashing light in recognition of a threshold value having been sensed. It will be understood that recognition of a threshold value being sensed with respect to one of the signals does not require that a threshold value has been reached with respect to the other signal, and that the visible light emitter associated with the threshold condition may emit visibly flashing light while another visible light emitter may not.

If the CNIBP and $SpO_2$ signals are determined not to have reached threshold values that would warrant alerting the sensor's user, then process 800 may advance to steps 819 and 823 for the CNIBP parameter, and steps 824 and 828 for the $SpO_2$ parameter, respectively, where the monitor transmits a drive signal to the sensor to drive the visible light emitters to emit light that is color-coded to represent the physiological parameters being monitored. The emission of colored light that appears constant to a user may indicate to the user of the sensor that the sensor is functioning normally and that neither the patient nor the sensor is experiencing a threshold condition.

The foregoing is merely illustrative of the principles of this disclosure and various modifications can be made by those skilled in the art without departing from the scope and spirit of the disclosure. The following claims may also describe various aspects of this disclosure.

What is claimed is:

1. A sensor for sensing physical characteristics of a patient, the sensor comprising:
    a support structure; and
    a sensor component coupled to the support structure for sensing a physical characteristic of the patient, wherein the sensor component is configured to:
        generate a physiological signal indicative of the physical characteristic;
        transmit the physiological signal to a monitor external to the sensor, wherein the physiological signal is capable of being used by the external monitor to monitor first and second physiological parameters;
        receive a first drive signal from the external monitor indicating when the external monitor is using the physiological signal to monitor the first physiological parameter; and
        receive a second drive signal from the external monitor indicating when the external monitor is using the physiological signal to monitor the second physiological parameter, the sensor component comprising:
            an infrared light emitter, wherein the infrared light is used to sense the physical characteristic;
            a detector for detecting the infrared light after it passes within the tissue of the patient;
            a first visible light emitter that emits visible light of a first color, wherein:
                the first visible light emitter is not used to sense the physical characteristic;
                the first color is color-coded to the first physiological parameter; and
                the first visible light emitter emits visible light in response to the sensor component receiving the first drive signal indicating when the external monitor is using the physiological signal to monitor the first physiological parameter; and
            a second visible light emitter that emits visible light of a second color, wherein:
                the second visible light emitter is not used to sense the physical characteristic;
                the second color is color-coded to the second physiological parameter; and
                the second visible light emitter emits visible light in response to the sensor component receiving the second drive signal indicating when the external monitor is using the physiological signal to monitor the second physiological parameter.

2. The sensor of claim 1 wherein the first physiological parameter comprises blood pressure, respiration rate, and/or respiration effort.

3. The sensor of claim 1 wherein the first visible light emitter emits visibly flashing light when the external monitor determines that the physical characteristic sensed by the sensor component for the first physiological parameter has reached a threshold.

4. The sensor of claim 1 wherein the first and second colors mix to appear as a third color that is color-coded to the first physiological parameter and the second physiological parameter.

5. The sensor of claim 4 wherein the third color appears to visibly flash when the external monitor determines that the physical characteristic sensed by the sensor component for the first physiological parameter and the second physiological parameter has reached a threshold.

6. The sensor of claim 1 wherein the second visible light emitter emits visibly flashing light when the external monitor determines that the physical characteristic sensed by the sensor component for the second physiological parameter has reached a threshold.

7. The sensor of claim 1 wherein the second visible light emitter emits light independently of the light emitted by the first visible light emitter.

8. The sensor of claim 1 wherein:
    the sensor component further comprises a third light emitter, wherein:
        the light emitted by the third light emitter is used to sense the first physical characteristic and/or a second physical characteristic used to monitor the first physiological parameter and/or the second physiological parameter; and
        the light emitted by the third light emitter is of a frequency that is different than the frequency of the visible light of a first color; and
    the detector detects the light emitted by the third light emitter after it passes within the tissue of the patient.

9. A method for visibly indicating the monitoring of a first physiological parameter of a patient and a second physiological parameter of the patient, the method comprising:
    sensing a first physical characteristic with a sensor that comprises a support structure and a sensor component coupled to the support structure, wherein the sensor component comprises an infrared light emitter, a detector, a first visible light emitter, and a second visible light emitter, and further wherein:
        the infrared light is used to sense the first physical characteristic; and
        the detector is used to detect the infrared light after it passes within the tissue of the patient;
    generating a physiological signal indicative of the first physical characteristic;
    transmitting the physiological signal to a monitor external to the sensor, wherein the physiological signal is capable of being used by the external monitor to monitor the first and second physiological parameters;
    receiving a first drive signal from the external monitor indicating when the external monitor is using the physiological signal to monitor the first physiological parameter;
    receiving a second drive signal from the external monitor indicating when the external monitor is using the physiological signal to monitor the second physiological parameter;
    visibly indicating the monitoring of the first physiological parameter by the external monitor with the first visible light emitter that emits visible light of a first color in response to receiving the first drive signal indicating when the external monitor is using the physiological signal to monitor the first physiological parameter, wherein:
        the first visible light emitter is not used to sense the first physical characteristic; and
        the first color is color-coded to the first physiological parameter; and
    visibly indicating the monitoring of the second physiological parameter by the external monitor with the second visible light emitter that emits visible light of a second color in response to receiving the second drive signal indicating when the external monitor is using the physiological signal to monitor the second physiological parameter, wherein:
the second visible light emitter is not used to sense the second physical characteristic; and
the second color is color-coded to the second physiological parameter.

10. The method of claim 9 further comprising visibly flashing the first visible light emitter in response to the sensor component sensing a threshold value of the first physical characteristic.

11. The method of claim 9 wherein the monitoring of the first and second physiological parameters is indicated by a visible combination of the first and second colors.

12. The method of claim 9 further comprising:
visibly flashing the first visible light emitter in response to the sensor component sensing a threshold value of the first physical characteristic; and
visibly flashing the second visible light emitter in response to the sensor component sensing a threshold value of the first physical characteristic and/or the second physical characteristic, wherein the first visible light emitter visibly flashes independently of the second visible light emitter.

13. A computer-readable medium for use in visibly indicating the monitoring of a first physiological parameter and a second physiological parameter, the computer-readable medium having computer program instructions recorded thereon for:
sensing a physical characteristic with a sensor that comprises a support structure and a sensor component coupled to the support structure, wherein the sensor component comprises an infrared light emitter, a detector, a first visible light emitter, and a second visible light emitter, and further wherein:
the infrared light is used to sense the physical characteristic; and
the detector is used to detect the infrared light after it passes within the tissue of the patient;
generating a physiological signal indicative of the physical characteristic;
transmitting the physiological signal to a monitor external to the sensor, wherein the physiological signal is capable of being used by the external monitor to monitor the first and second physiological parameters;
receiving a first drive signal from the external monitor indicating when the external monitor is using the physiological signal to monitor the first physiological parameter;
receiving a second drive signal from the external monitor indicating when the external monitor is using the physiological signal to monitor the second physiological parameter;
visibly indicating the monitoring of the first physiological parameter by the external monitor with the first visible light emitter that emits visible light of a first color in response to receiving the first drive signal indicating when the external monitor is using the physiological signal to monitor the first physiological parameter, wherein:
the first visible light emitter is not used to sense the physical characteristic; and
the first color is color-coded to the first physiological parameter; and
visibly indicating the monitoring of the second physiological parameter by the external monitor with the second visible light emitter that emits visible light of a second color in response to receiving the second drive signal indicating when the external monitor is using the physiological signal to monitor the second physiological parameter, wherein:
the second visible light emitter is not used to sense the second physical characteristic; and
the second color is color-coded to the second physiological parameter.

* * * * *